United States Patent [19]
Ray

[11] 3,936,736
[45] Feb. 3, 1976

[54] RADOME TEST INSTRUMENT
[75] Inventor: N. Reece Ray, Marietta, Ga.
[73] Assignee: Lockheed Aircraft Corporation, Burbank, Calif.
[22] Filed: Aug. 28, 1974
[21] Appl. No.: 501,038

[52] U.S. Cl.... 324/58.5 R; 324/58.5 A; 324/58.5 B; 324/58 B
[51] Int. Cl.[2] .......................................... G01R 27/04
[58] Field of Search ..... 324/58.5 R, 58.5 A, 58.5 B, 324/58.5 C, 58 B

[56] References Cited
UNITED STATES PATENTS

| | | | |
|---|---|---|---|
| 3,025,463 | 3/1962 | Luoma et al. | 324/58.5 B |
| 3,786,330 | 1/1974 | Inoue et al. | 324/58.5 B |
| 3,789,296 | 1/1974 | Caruso, Jr. et al. | 324/58.5 B |
| 3,836,846 | 9/1974 | Overall et al. | 324/58.5 B |
| 3,853,005 | 12/1974 | Schendel et al. | 324/58.5 B |

OTHER PUBLICATIONS
"Polarisation of E.M. Waves Scattered by Water Drops," by Dunlopetal, Electronics Letters, Vol. 7, No. 3, 2/71, pp. 87 & 88.

Primary Examiner—Saxfield Chatmon, Jr.
Attorney, Agent, or Firm—Billy G. Corber; John J. Sullivan

[57] ABSTRACT

This hand held universal radome tester is an instrument for locating discontinuities and impurities inside a radome wall and for determining the quality of an anti-static paint coating over the exterior surface of a radome. It includes a microwave segment which is energized in the discontinuities/impurities mode of operation to measure energy reflected by the radome wall, and a dc segment which is energized in the anti-static paint tester mode to measure resistance in megohms per square. The tester is battery-operated making it a completely portable device.

9 Claims, 1 Drawing Figure

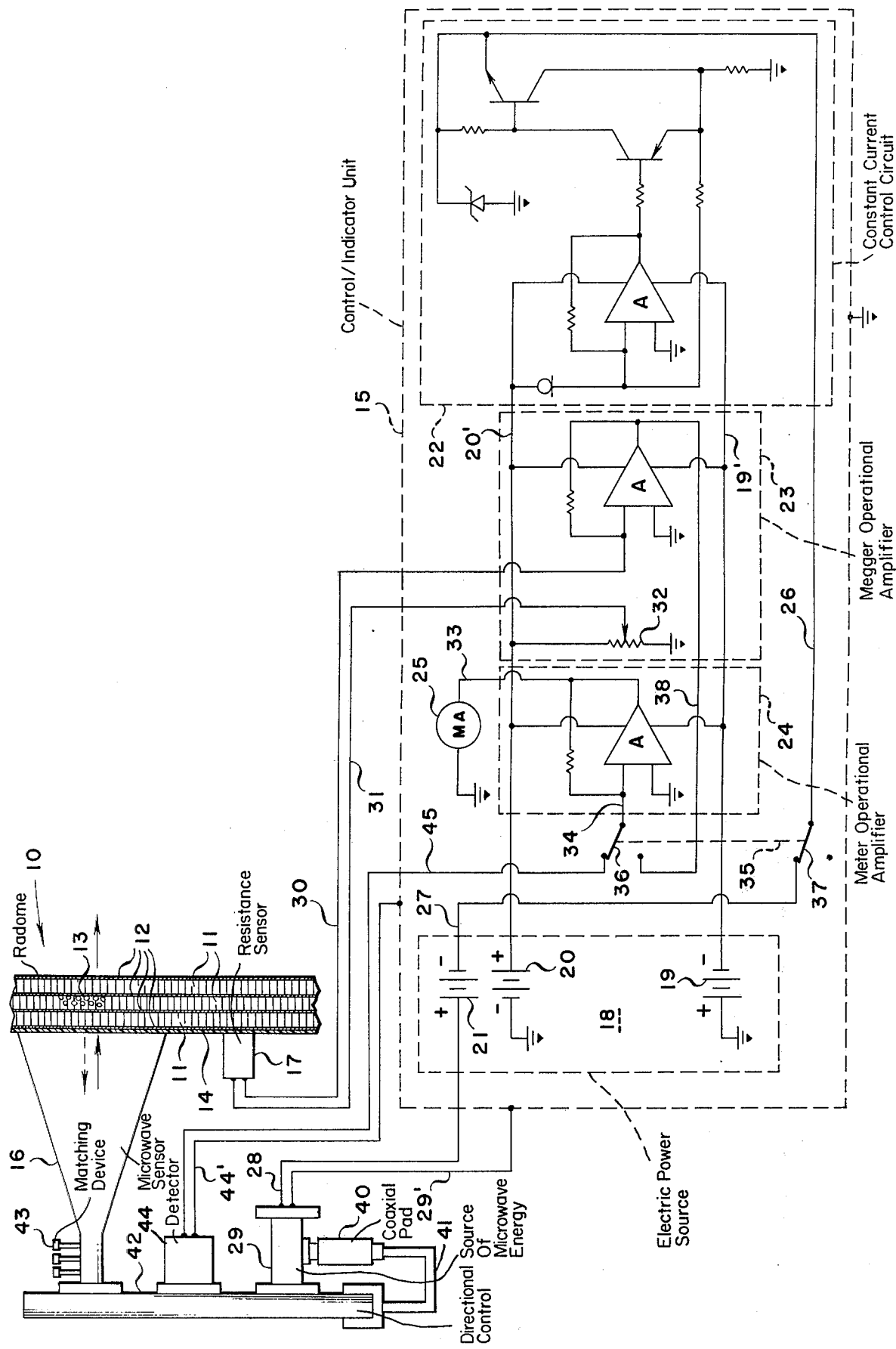

RADOME TEST INSTRUMENT

This invention relates generally to test mechanisms employed to examine equipment to assure the proper condition and operating efficiency thereof and more particularly to a test instrument for radomes to determine the signal transmission capabilities thereof and the quality of an electrically conductive coating over the exterior surface of such radomes.

Radomes, externally covered with an electrically conductive coating of antistatic paint, must efficiently pass microwave energy through their walls. Loss of the anti-static paint can cause static charge buildup on the radome surface resulting in precipitation static (P-static) interfering with the operation of nearby radio equipment. Also, the presence of foreign matter, such as for example water, within the radome wall causes a decrease in transmission efficiency and excessive bore-sight shift.

During the life of the radome, the anti-static paint and then the exterior radome surface, gradually erodes or wears away and physical damage caused by such things as rain, hail and the like allows water to penetrate the radome wall. Thus, discrepancies in the radome transmission properties occur which must be corrected by removing any water or other impurities, patching damaged areas and externally recoating the radome.

The present invention, therefore, proposes an instrument to check for properties which can adversely affect the electrical characteristics of radomes. This permits better quality control of radomes at the time of their manufacture as well as field checking of radomes to the end that the deterioration thereof below some established level can be detected and corrected promptly as a routine matter. This device can detect the condition of anti-static paint, the presence of impurities such as water, resin heavy areas, areas with thick skins and improperly patched areas in a radome.

To the above ends the test instrument herein proposed comprises a source of power, a pair of sensors, electrical circuits individually and selectively connectable between the power source and each of the sensors, a detector associated with each sensor to pick up energy passing through the connected sensor and an indicator responsive to this detected energy. Adjustable means is included to regulate the magnitude of the power from the source to the sensors as well as the energy being indicated.

More specifically, the power to one of the sensors is in the form of microwave energy which is adapted to be transmitted or radiated by that sensor and a detector is provided to receive any reflected energy from a radome under test and to actuate an associated device accordingly as, for example, by registering this on an associated indicator or meter. The power from the source to the other sensor is in the form of electric current which is adapted to be short circuited by that sensor with the resulting resistance being registered on the associated meter. By establishing the tolerable levels of reflected energy and resistance, indications in excess of these levels can be rejected.

Devices operating on the radar principle, as contemplated herein, using the detection of the magnitude of a reflected wave to indicate the presence and quantity of non-uniformities in material have been heretofore proposed. Typical of such prior art devices is that disclosed by the Inoue et al U.S. Pat. No. 3,786,330 issued Jan. 15, 1974. Inoue et al provides a windshield wiping apparatus which uses the differential transmission of microwave energy through a car windshield to detect water on the external surface thereof. In contrast, the underlying concept of the present invention is the measurement in the difference in reflected energy by a dielectri material in order to detect impurities inside th dielectric, i.e., radome.

It has also been proposed to locate defects in glass using the doppler frequency shift technique as taught by the Slobodsky U.S. Pat. No. 3,144,601 issued Aug. 11, 1964. This known concept requires precise, relative movement between the test instrument and the test article and consequently involves additional rather complex apparatus. By employing the amplitude of reflected energy only, as herein contemplated, such complications are avoided and portabaility is more readily attained.

Other known devices in the general area to which this invention relates are disclosed in the following patents:

| | | |
|---|---|---|
| Kofoid | 2,952,296 | Issued September 13, 1960 |
| Hanson et al | 3,278,841 | Issued October 11, 1966 |
| Chafee | 3,290,587 | Issued December 6, 1966 |
| Prine | 3,482,160 | Issued December 2, 1969 |
| Caruso et al | 3,789,296 | Issued January 29, 1974 |

None of the devices contemplated by the foregoing prior art, however, can detect water and other impurities or discontinuities within a radome wall. Nor can any of these existing devices be used effectively on a radome covered with antistatic paint or on multi-sandwich radomes.

With the above and other objects in view as will become apparent, this invention consists in the construction, combination and arrangement of parts all as hereinafter more fully described, claimed, and illustrated in the accompanying drawing, wherein a schematic arrangement of a radome test instrument within the purview of the present invention is shown located adjacent a radome wall under test, only a fragment of the radome wall being illustrated and in section.

Referring more particularly to the drawing, 10 designates a typical radome of multilayer sandwich construction formed by three honeycomb core sections 11 and four fiberglass sheets 12 bonded together into an integral structure. Impurities, for example localized water droplets 13, are illustrated within the honeycomb 11 but otherwise the radome 10 is uniform throughout, being intended by design and construction to pass a prescribed frequency or multi-frequencies to associated equipment (not shown). The outer surface of the radome 10 is covered with a coating 14 of electrically conductive paint adapted to bleed off static charges which otherwise tend to build up on the surface and discharge into radio receiving equipment in the near vicinity.

The instrument herein proposed to test the operating efficiency of the radome 10 consists essentially of a control/indicator unit 15 with a pair of sensors 16 and 17 connected thereto and extending therefrom. The control/indicator unit 15 contains a power source preferably in the form of a rechargeable battery pack 18 which includes a pair of relatively low voltage, e.g. 12v, batteries 19 and 20, and a relatively high voltage, e.g. 120v, battery 21, a constant current control circuit 22, a megger operational amplifier 23 and a meter operational amplifier 24 connected to an indicator or meter 25 having a face or dial readable from the exterior of the unit 15.

The batteries 19 and 20 are each grounded at opposite poles and connected at their other opposite poles through leads 19' and 20', respectively, thereby providing power to the constant current control circuit 22, the megger operational amplifier 23 and the meter operational amplifier 24. The output of the constant current control circuit 22 is connectable through conductors 26 and 27 to the negative pole of the battery 21. The positive pole of the battery 21 connects through a conductor 28 to an oscillator, e.g. an X-band solid state or an impatt diode 29, grounded through a lead 29' to the circuit ground of the unit 15.

The megger operational amplifier 23 within the unit 15 is connected by a conductor 30 to the sensor 17 and serves to measure the resistance of the conductive coating 14. A conductor 31 connects the sensor 17 to a potentiometer 32 also housed within the unit 15. This potentiometer 32 permits an adjusted voltage value in the sensor 17 for reasons to become more apparent.

Finally, the meter operational amplifier 24 within the unit 15 is connected at one of its ends by a conductor 33 to the meter 25 and by a conductor 34 to a switch mechanism 35 at its other end. The switch mechanism 35 includes a pair of gang connected switching elements 36 and 37. The switch 36 has alternate positions whereby the indicator or meter 25 is either connected to the microwave sensor 16 or to the resistance sensor 17. The switch 37 has alternate positions whereby the microwave oscillator constant current control circuit 22 is either connected through the leads 26 and 27 to the battery 21 or through lead 26 alone to open circuit. The operation of the mechanism 35 is such that when the megger operational amplifier circuit 23 is connected to the meter 25 through a conductor 38 and the meter operational amplifier 24, the oscillator constant current control circuit 22 is disconnected from the battery 21 and open-circuited.

With the circuit 23 thus connected and the terminals of the sensor 17 shortcircuited, the potentiometer 32 is adjusted to give full scale deflection on the meter 25. As in the case of a standard voltohmeter, a full scale meter deflection represents zero resistance and a zero meter deflection from a near-open circuit indicates infinite resistance. Through the selection of resistors in the circuit 23 the meter 25 is calibrated to allow more accurate measurements in the low megohm region (1 to 10), the high megohm region (100 to 500), or the middle range (10 to 100). The sensor 17 is a probe with one terminal entirely encircling the other to allow megohms per square measurements of the anti-static paint rather than point-to-point megohms.

In the alternate position of the switching mechanism 35, i.e., the position illustrated with the microwave sensor 16 connected to the meter 25, the battery 21 energizes the oscillator 29 transmitting the CW (continuous wave) of microwave energy through a coaxial pad 40 which serves to stabilize the load on the oscillator 29, down a coaxial cable 41 and into a directional control in the form of a printed board or more specifically a stripline ring hybrid 42. This microwave energy passes through the stripline ring hybrid 42 through a matching device, e.g. a triple stub tuner 43 (which allows the adjustment of the impedance of the microwave sensor 16) and into the sensor 16 from which it is transmitted into the multi-sandwich radome wall 10 under test, as indicated by the solid line arrows.

As indicated by the broken line arrow, some of the energy thus transmitted into the wall 10 is reflected back into the sensor 16. The amount of reflected energy is dependent upon the design of the wall 10 and the presence of any impurity or discontinuity such as water 13 in the wall 10. The reflected energy passes back into the ring hybrid 42 and then into a detector, e.g. a crystal mount 44 (grounded as at 44'), through a lead 45, switch 36 and conductor 34 to the meter 25. The amount of this reflected energy is dependent upon the initial setting of the tuner 43.

The initial tuner setting establishes two methods of using the system to detect impurities 13:

1. Freespace Reference — With the sensor 16 pointed into free space, the triple stub tuner 43 is adjusted for a null reading on meter 25. Under this condition, the sensor 16 is matched and no microwave energy is reflected back into the detector 44. The sensor 16 is then placed flush against the surface of the radome wall 10. This results in only a small mismatch of the aperture for most properly designed and constructed X-band radomes. This is taken into consideration during calibration and usage. When an impurity or water droplet 13 is encountered, the sensor 16 is further mismatched resulting in reflected energy into the detector 44 and corresponding deflection of the meter 25.

2. Sample Panel Reference — The sensor 16 is initially placed flush against the surface of an impurities-free and discontinuities-free sample panel of the radome to be tested. Tuner 43 is adjusted for a null reading on the meter 25. The sensor 16 is then placed against the surface of the radome wall 10 under test. No indication is noted unless an impurity or discontinuity such as water droplets 13 is encountered. With the switch mechanism 35 in the position illustrated, the reflected signal is rectified in detector 44 and fed through the lead 45, switch 36, conductor 34, circuit 24 and into the meter 25. The degree of the meter deflection is determined by the magnitude of the impurity or discontinuity of the radome wall 10 and is controlled by the amplitude of the transmitted microwave energy, the sensitivity of the detector 44 and the gain of the amplifier within the circuit 24. All of these variables are taken into consideration when calibrating the meter 25.

In using either of the methods described above, the meter 25 is calibrated for a no-go zone wherein meter deflection above a certain value registers an unacceptable condition for the radome 10 in the particular area being investigated. The no-go zone will vary with radome design and will have to be established for each type of radome to be tested.

The present invention has been shown and described in what is believed to be the most practical and preferred embodiment whereby it can be readily practiced by those skilled in the art to which it pertains. It is apparent that variations of the specific structures disclosed will suggest themselves to those skilled in the art and may be made without departing from the spirit and scope of the invention as fairly defined by the appended claims.

What is claimed is:

1. A test instrument for radomes of multilayer sandwich construction designed to pass a prescribed frequency and having an outer surface covered with a coating of electrically conductive paint adapted to bleed-off static charges thereon comprising:
- a microwave sensor adapted to be placed against the surface of a radome wall;
- a first electrical circuit including said microwave sensor, a source of microwave energy, a matching device to adjust the impedance of said microwave sensor to a predetermined value, a detector, a directional control for the flow of energy from said microwave energy source to said microwave sensor and the flow of reflected energy from said radome wall to said detector corresponding to variations from said predetermined value and an indicator connected to said detector and operable in response to the reflected energy aforesaid;
- a resistance sensor adapted to be placed against said outer surface of said radome wall;
- a second electrical circuit including said resistance sensor, a source of electrical energy, an amplifier and the indicator aforesaid; and
- a selector switch common to said first and second electrical circuits and operative to connect one of said circuits to, and concurrently disconnect the other of said circuits from, said indicator.

2. The instrument of claim 1 including a potentiometer in said second electrical circuit operable to adjust the voltage value thereof.

3. The test instrument of claim 1 wherein said source of microwave energy is an oscillator and said directional control is a stripline ring hybrid and including a coaxial pad and a coaxial cable operatively connected therebetween.

4. The test instrument of claim 3 wherein said detector is a crystal mount.

5. The test instrument of claim 1 wherein said indicator is a milliampmeter and includes a meter operational amplifier associated therewith.

6. The test instrument of claim 1 wherein said first circuit includes a constant current control circuit.

7. The test instrument of claim 1 wherein said amplifier is a megger operational amplifier.

8. The test instrument of claim 7 wherein said first circuit includes a constant current control circuit, wherein said source of microwave energy includes a rechargeable battery pack and wherein said constant current control circuit, said megger operational amplifier, said indicator and said battery pack are all housed within a common container with said microwave and resistance sensors extending therefrom.

9. The test instrument of claim 1 wherein said source of electrical energy is a rechargeable battery pack.

* * * * *